United States Patent
Dart

(10) Patent No.: US 11,360,091 B2
(45) Date of Patent: Jun. 14, 2022

(54) METHOD FOR DIAGNOSIS, PROGNOSIS OR TREATMENT OF ACUTE CORONARY SYNDROME (ACS) COMPRISING MEASUREMENT OF PLASMA CONCENTRATION OF MACROPHAGE MIGRATION INHIBITORY FACTOR (MIF)

(71) Applicants: Alfred Health, Melbourne (AU); Baker IDI Heart and Diabetes Institute Holdings LTD, Melbourne (AU)

(72) Inventor: Anthony Dart, Melbourne (AU)

(73) Assignees: ALFRED HEALTH, Melbourne (AU); BAKER IDI HEART AND DIABETES INSTITUT HOLDINGS LTD., Melbourne (AU)

(*) Notice: Subject to any disclaimer, the term of this patent is extended or adjusted under 35 U.S.C. 154(b) by 60 days.

(21) Appl. No.: 14/178,660

(22) Filed: Feb. 12, 2014

(65) Prior Publication Data
US 2014/0234861 A1    Aug. 21, 2014

Related U.S. Application Data

(63) Continuation of application No. PCT/AU2011/001027, filed on Aug. 12, 2011.

(51) Int. Cl.
G01N 33/68    (2006.01)
G01N 33/573   (2006.01)
G01N 27/28    (2006.01)

(52) U.S. Cl.
CPC ............ *G01N 33/573* (2013.01); *G01N 27/28* (2013.01); *G01N 33/6863* (2013.01); *G01N 2800/324* (2013.01)

(58) Field of Classification Search
None
See application file for complete search history.

(56) References Cited

U.S. PATENT DOCUMENTS

2005/0054117 A1* 3/2005 Giroir et al. .................. 436/518
2006/0034832 A1* 2/2006 Kimura et al. ............. 424/133.1
2011/0144914 A1  6/2011 Harrington et al.

FOREIGN PATENT DOCUMENTS

| WO | 2006001813 | 1/2006 |
| WO | 2007/140188 A2 | 12/2007 |
| WO | WO 2009/017405 A2 | 2/2009 |
| WO | 2019/060960 A1 | 4/2019 |
| WO | 2019/061396 A1 | 4/2019 |

OTHER PUBLICATIONS

Walker et al (J Am Soc Nephrol. Jan. 2012; 23(1): 13-21).*
Mayeux (NeuroRx. Apr. 2004;1(2):182-8) (Year: 2004).*
Sprang et al (SHOCK, vol. 27, No. 5, pp. 482-487, 2007) (Year: 2007).*
Zhao et al (Int J Cancer. Nov. 15, 2011;129(10):2463-72. Epub Apr. 20, 2011.) (Year: 2011).*
Dandona etal (J Clin Endocrinol Metab. Oct. 2004;89(10):5043-7) (Year: 2004).*
International Preliminary Report on Patentability from the Australian Patent Office for International Application No. PCT/AU2011/001027 dated Dec. 10, 2013 (5 pages).
International Search Report for International Application No. PCT/AU2011/001027 dated Sep. 14, 2011 (2 pages).
Yu, C. et al., Elevation of plasma concentration of macrophage migration inhibitory factor in patients with acute myocardial infarction, American Journal of Cardiology 2001, 88:774-777.
Achar, S. et al., Diagnosis of Acute Coronary Syndrome, American Family Physician 2005, vol. 72, pp. 119-126.
Than, M. et al., A 2-h diagnostic protocol to assess patientsd with chest pain symptoms in the Asia-Pacific region (ASPECT): a prospective observational validation study, Lancet 2011, 88(7):774-777.
McCord, J. et al., Ninety-minute exclusion of acute myocardial infarction by use of quantitative point-of-care testing of myoglobin and troponin, i. Circulation. 2001, 104(13):1483-1488.
Ganame, J. et al., Impact of myocardial haemorrhage on left ventricular function and remodelling in patients with reperfused acute myocardial infarction, European Heart Journal 2009, 30(12):1440-1449.
Piot, C. et al., Effect of cyclosporine on reperfusion injury in acute myocardial infarction, New England Journal of Medicine 2008, 359(5):473-481.
Chan, W., et al; Macrophage migration inhibitory factor or the early prediction of infarct size; Jour. Amer. Heart Assoc.; 2013; 2.5; e000226.
Chan, W., et al; Acute left ventricular remodeling following myocardial infarction: coupling of regional healing with remote extracellular matrix expansion; JACC: Cardiovascular Imaging; 2012; 5.9; 884-893.

(Continued)

*Primary Examiner* — Brian Gangle
*Assistant Examiner* — Andrea K McCollum
(74) *Attorney, Agent, or Firm* — Kilpatrick Townsend & Stockton LLP

(57) ABSTRACT

A method for diagnosing acute coronary syndrome (ACS) in a subject, the method comprising measuring plasma macrophage migration inhibitory factor (MIF) concentration in a sample from the subject, and diagnosing ACS when the subject plasma MIF concentration is greater than a reference plasma MIF concentration, wherein the sample is taken less than 4 hours after symptom onset. The invention also relates to a method for prognosing ACS in a subject, the method comprising measuring plasma MIF concentration in a sample from the subject, diagnosing ACS when the subject plasma MIF concentration is greater than a reference plasma MIF concentration, and prognosing the magnitude of ACS from the subject plasma MIF concentration. Also provided is a method of treating ACS in a subject, a device, a kit, and a cardiac biomarker related to the methods of diagnosing and prognosing ACS.

9 Claims, 5 Drawing Sheets

Specification includes a Sequence Listing.

(56) References Cited

OTHER PUBLICATIONS

Cho, et al; The Utility of point-of-care biomarkers as a prognostic tool for patients with acute coronary syndromes; Signa Vitae; 2017; 13(1); 89-94.

Deng, X.-N., et al; Admission macrophage migration inhibitory factor predicts long-term prognosis in patients with ST-elevation myocardial infarction; Eur. Heart Jour.—Quality of Care and Clinical Outcomes; Jul. 1, 2018; (published online: May 2, 2018), 4.3, 208-219.

Deng, X.-N., et al; Admission macrophage migration inhibitory factor predicts long-term prognosis in patients with ST-segment elevation myocardial infarction; Jour. Amer. College of Cardiology; Mar. 20, 2018; 71.11; Suppl. A240, Presentation No. 1305-451.

Gao, X., et al; Macrophage migration inhibitory factor (MIF), a novel biomarker and player in acute myocardial infarction (AMI); Heart, Lung and Circulation; 2012; 21 Suppl. S44, Abstract 104.

Li, M., et al; Macrophage migration inhibitory factor in predicting short-and long-term major adverse cardiovascular events in patents with ST-segment elevation myocardial infarction; Jour. Amer. College of Cardiology; 2014; 64, 16, Suppl. C, C61, Abstract GW25-e2515.

Seropian, I., et al; Inflammatory markers in ST-elevation acute myocardial infarction; Eur. Heart Jour.: Acute Cardiovascular Care; 2016 5.4, 382-395.

Tuxunguli, T., et al; Association study of plasma NT-proBNP levels and severity of acute syndrome; Genet. Mol. Res.; 2014; 13(3): 5754-5757.

\* cited by examiner

SEQUENCE LISTING

<160> NUMBER OF SEQ ID NOS: 1

<210> SEQ ID NO 1
<211> LENGTH: 115
<212> TYPE: PRT
<213> ORGANISM: Homo sapiens

<400> SEQUENCE: 1

Met Pro Met Phe Ile Val Asn Thr Asn Val Pro Arg Ala Ser Val Pro
1               5                   10                  15

Asp Gly Phe Leu Ser Glu Leu Thr Gln Gln Leu Ala Gln Ala Thr Gly
            20                  25                  30

```
Lys Pro Pro Gln Tyr Ile Ala Val His Val Val Pro Asp Gln Leu Met
    35                  40                  45
Ala Phe Gly Gly Ser Ser Glu Pro Cys Ala Leu Cys Ser Leu His Ser
    50                  55                  60
Ile Gly Lys Ile Gly Gly Ala Gln Asn Arg Ser Tyr Ser Lys Leu Leu
65          70                  75                      80
Cys Gly Leu Leu Ala Glu Arg Leu Arg Ile Ser Pro Asp Arg Val Tyr
            85                  90                  95
Ile Asn Tyr Tyr Asp Met Asn Ala Ala Asn Val Gly Trp Asn Asn Ser
            100             105             110
Thr Phe Ala
    115
```

METHOD FOR DIAGNOSIS, PROGNOSIS OR TREATMENT OF ACUTE CORONARY SYNDROME (ACS) COMPRISING MEASUREMENT OF PLASMA CONCENTRATION OF MACROPHAGE MIGRATION INHIBITORY FACTOR (MIF)

CROSS-REFERENCE TO RELATED APPLICATIONS

This application is a continuation of International Patent Application No. PCT/AU2011/001027, filed on Aug. 12, 2011, the disclosure of which is incorporated by reference herein in its entirety for all purposes.

SEQUENCE LISTING

The instant application contains a Sequence Listing which has been submitted electronically in ASCII format and is hereby incorporated by reference in its entirety. Said ASCII copy, created on Mar. 18, 2014, is named 14963955 ASFILED SequenceListing-Text.txt and is 1.49 KB in size.

BACKGROUND OF THE INVENTION

The invention relates to a method for diagnosing acute coronary syndrome (ACS), a method for prognosing ACS, and a cardiac biomarker for use in the methods. The invention also relates to a device and a kit for use according to the methods.

It is to be understood that, if any prior art publication is referred to herein, such reference does not constitute an admission that the publication forms a part of the common general knowledge in the art, in Australia or any other country.

The use of plasma biomarkers has become central to the diagnosis and management of ACS. For example, the prognostic impact of troponin elevation among patients with coronary artery disease (CAD) is well established.

Existing plasma biomarkers for myocardial necrosis and hence ACS include myoglobin, creatine kinase (CK), and troponin. Each of these plasma biomarkers is problematic.

Myoglobin peaks in plasma approximately 2 hours after a cardiac event. However, myoglobin has low cardiac-specificity.

Peak plasma CK and cumulative release (area under the curve) of CK may be used to diagnose ACS, including calculation of infarct size due to myocardial necrosis. CK peaks in plasma approximately 10 hours after a cardiac event. Cumulative plasma CK concentrations are not available until at least 48 hours after the cardiac event. Furthermore, CK is not cardiac-specific.

Troponin has become the predominantly used plasma biomarker for the early detection of ACS, for example myocardial necrosis, and has largely superseded the measurement of CK. Troponin is the most sensitive and specific test for myocardial necrosis at present. Peak plasma troponin and cumulative release of troponin both may be used to diagnose ACS, including calculation of infarct size due to myocardial necrosis. However, apparent elevation in plasma troponin due to non-coronary (non-ischaemic) causes is well known, such as due to the presence of renal failure, sepsis or heterophile antibodies. Although these limitations are important, the most significant limitation to the diagnostic value of plasma troponin measurements is the delay between the onset of a cardiac event and the subsequent elevation in troponin. In many cases, no elevation in troponin is evident during the first 6 hours after a cardiac event. Therefore, to exclude or rule out ACS, e.g. AMI, on the basis of peak troponin concentrations, serial measurements up to 8 to 12 hours after symptom onset must be performed. Calculation of cumulative plasma troponin concentrations require measurements to be taken for at least 48 hours after the cardiac event.

Therefore, there is a need for a method for diagnosing ACS using a biomarker specific for ACS that can improve early, i.e. less than 6 hours after symptom onset, diagnosis of patients presenting with chest pain. Such a method has the potential to critically affect global health-service delivery.

SUMMARY OF THE INVENTION

A first aspect provides a method for diagnosing acute coronary syndrome (ACS) in a subject, the method comprising measuring plasma macrophage migration inhibitory factor (MIF) concentration in a sample from the subject, and diagnosing ACS when the subject plasma MIF concentration is greater than a reference plasma MIF concentration, wherein the sample is taken less than 4 hours after symptom onset.

A second aspect provides a method for prognosing ACS in a subject, the method comprising measuring plasma MIF concentration in a sample from the subject, diagnosing ACS when the subject plasma MIF concentration is greater than a reference plasma MIF concentration, and prognosing the magnitude of ACS from the subject plasma MIF concentration.

A third aspect provides a method of treating ACS in a subject, the method comprising: (a) measuring plasma MIF concentration in a sample taken from the subject less than 4 hours after symptom onset, and diagnosing ACS when the subject plasma MIF concentration is greater than a reference plasma MIF concentration; or (b) measuring plasma MIF concentration in the subject sample, diagnosing ACS when the subject plasma MIF concentration is greater than the reference plasma MIF concentration, and prognosing the magnitude of ACS from the subject plasma MIF concentration; and (c) performing percutaneous coronary intervention (PCI) and/or fibrinolysis on the subject.

A fourth aspect provides a device comprising means for measuring plasma MIF concentration in a sample from a subject, for use in a method for: (a) diagnosing ACS in the subject, the method comprising measuring plasma MIF concentration in the sample taken from the subject less than 4 hours after symptom onset, and diagnosing ACS when the subject plasma MIF concentration is greater than a reference plasma MIF concentration; or (b) prognosing ACS in the subject, the method comprising measuring plasma MIF concentration in the sample, diagnosing ACS when the subject plasma MIF concentration is greater than a reference plasma MIF concentration, and prognosing the magnitude of ACS from the subject plasma MIF concentration.

A fifth aspect provides a kit comprising a reagent for measuring plasma MIF concentration in a sample from a subject, for use in a method for: (a) diagnosing ACS in the subject, the method comprising measuring plasma MIF concentration in the sample taken from the subject less than 4 hours after symptom onset, and diagnosing ACS when the subject plasma MIF concentration is greater than a reference plasma MIF concentration; or (b) prognosing ACS in the subject, the method comprising measuring plasma MIF concentration in the sample, diagnosing ACS when the subject plasma MIF concentration is greater than a reference plasma MIF concentration, and prognosing the magnitude of ACS from the subject plasma MIF concentration; and/or comprising the device of the fourth aspect.

A sixth aspect provides a cardiac biomarker comprising plasma MIF concentration in a sample taken from a subject less than 4 hours after symptom onset, wherein plasma MIF concentration greater than a reference plasma MIF concentration is diagnostic of ACS in the subject.

A seventh aspect provides a cardiac biomarker comprising plasma MIF concentration in a sample from a subject, wherein plasma MIF concentration greater than a reference plasma MIF concentration is prognostic of the magnitude of ACS in the subject.

The inventors were studying the effects of iron chelation with desferrioxamine on infarct size in patients with STEMI, and elected to measure plasma MIF concentrations and infarct size. MIF is a known protein. MIF is also known to be released into plasma within 1 day after AMI. Surprisingly, the inventors found that MIF concentrations were diagnostic of AMI, when MIF was measured in plasma samples taken from AMI subjects less than 4 hours after AMI (symptom onset). Furthermore, the inventors unexpectedly found that, not only were such plasma MIF concentrations diagnostic for AMI, the plasma MIF concentrations were also prognostic for the magnitude of AMI, i.e. infarct size. The inventors validated their findings and the resulting invention provides at least the following advantages over the methods and biomarkers of the prior art.

(1) at present, myoglobin is the earliest measure of infarction, but myoglobin is neither cardiac specific nor does it prognose or predict infarct size, whereas plasma MIF is both cardiac specific and prognostic of infarct size;
(2) MIF appears in the plasma less than 4 hours after symptom onset, similar to myoglobin but much earlier than CK and troponin;
(3) MIF concentration measured in plasma taken less than 4 hours after symptom onset is diagnostic for ACS, whereas none of myoglobin, CK or troponin measured in plasma taken at similar time points is diagnostic for ACS; and
(4) plasma MIF concentration is prognostic of the magnitude or extent of MI and consequently morbidity and mortality (cf. all existing biomarkers).

DETAILED DESCRIPTION

Figure 1:
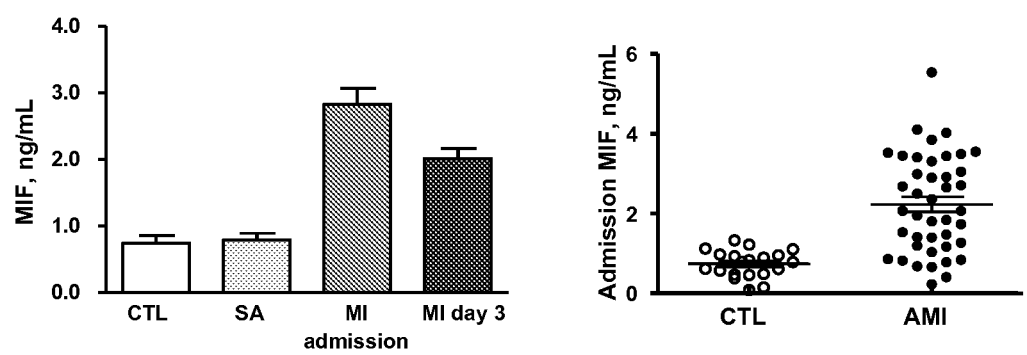
FIG. 1 depicts admission plasma MIF concentrations that were increased in subjects after AMI (MI, n=15), but not in subjects with stable angina (SA, n=10) or in healthy subjects (CTL, n=10). Plasma MIF concentrations were increased in patients with AMI also at day 3 (n=14) post infarct. *P<0.05 vs. CTL or SA, †P<0.05 vs. MI at day 1 (MI d1).

Long-term mortality and morbidity following AMI are largely determined by MI size, and the extent of left ventricular (LV) dysfunction. Primary percutaneous coronary intervention (PPCI) is now the established standard of treatment in patients with ST-elevation MI (STEMI) to limit infarct size and mortality. The inventors have found that admission plasma MIF concentrations greater than normal (i.e. a reference concentration) can diagnose AMI, particularly STEMI. Some subjects exhibit an abnormal ECG at baseline, which is uninformative for diagnosis of ACS or AMI. Therefore, admission plasma MIF concentrations are particularly useful for diagnosing AMI in these subjects.

Most subjects diagnosed with AMI are treated by PPCI. In hospitals lacking PCI facilities, either permanently or temporarily, the inventors propose that admission MIF plasma concentrations can establish whether or not a given subject should be transferred to a hospital with PCI facilities. Moreover, the inventors have found that MIF has prognostic impact, and accordingly early accurate prediction of MI size in patients with AMI is advantageous, particularly in complex patients, or where local health-care resources are limited.

Example 1 demonstrates that plasma MIF concentrations are elevated in a higher proportion of STEMI patients at the first obtainable sample post admission compared to other biomarkers. It is disclosed further that a single admission plasma MIF concentration is superior to current biomarkers for the early diagnosis of acute myocardial necrosis in STEMI given that MIF appears to be elevated very early post myocardial necrosis. It is also disclosed herein that plasma MIF concentration derived from the earliest blood sample obtainable after admission was able to accurately predict infarct size assessed by cardiac magnetic resonance (CMR), the current standard imaging modality for evaluation of infarct size and cardiac function.

There is, therefore, an inherent advantage in the availability of a biomarker, such as admission plasma MIF concentration, that can detect myocardial necrosis in the majority of patients within the first few hours of presentation to hospital, a time when plasma troponin concentrations remain within the normal range. As the inventors have shown, admission plasma MIF concentrations have implications for diagnosis, prognosis (i.e. by predicting infarct size) and patient management.

Studies with genetically modified animals have revealed a critical role for MIF in the orchestration of the intense inflammatory response following AMI. MIF is known to be present in a preformed state in cardiac myocytes. This is supported by human clinical studies that have reported markedly elevated MIF plasma concentrations detected as early as 4 to 6 hours after AMI, which remain elevated over the next 2 weeks before returning to control concentration 3 weeks following AMI. Although these clinical and experimental studies have indicated a close association between MIF and AMI, to what extent very early circulating MIF concentrations correlate with the onset and extent of myocardial necrosis, i.e. infarct size, has not been established. That is, until the present inventors demonstrated that MIF concentrations are elevated in less than 4 hours after symptom onset, and that plasma MIF concentrations are both diagnostic and prognostic of ACS (e.g. AMI and infarct size).

Limitation of MI size, whether by fibrinolysis or PCI is critical in reducing morbidity and mortality in STEMI. Early knowledge of the eventual MI size during the decision-making process about patient management and revascularization provides numerous advantages. Firstly, clinicians assessing patients in whom the diagnosis of STEMI is not obvious or stuttering may benefit from the knowledge that an elevated biomarker predicts MI size, which would facilitate the decision-making process about the timeliness of reperfusion, as well as post reperfusion supportive cardiac care required in coronary care unit or intensive care. Secondly, in regions where health-care resources are limited, early knowledge of the eventual MI size may influence whether to transport the patient to a PCI-capable hospital, or trial fibrinolysis first, especially in those with significant co-morbidities. The finding of an impressive correlation between a single admission plasma MIF concentration and day 3 MI size, a finding which persists at 3 months, proves that the present biomarker is useful in the clinical setting, especially in the emergency room setting, or integrated as another biomarker in the point-of-care panel. It is acknowledged that emergent mechanical reperfusion by PPCI is the goal in patients with STEMI. The measurement of admission plasma MIF concentration, which should not delay reperfusion, will be highly valuable in the ongoing management, including the use of adjunctive therapy, of patients post PPCI, as it provides further prognostic information on MI size.

Early diagnosis is critical to the management of patients with suspected ACS. Additionally, early knowledge of the eventual MI size is advantageous in prioritising patient management, and health-care delivery services. It is disclosed herein in Example 1 that admission plasma MIF concentrations were highest in patients with STEMI (STEMI 2.2±1.2 vs. stable CAD 0.8±0.3 vs. controls 0.7±0.4 µg/L, p<0.0001). Compared to myoglobin, cTnI and CK, plasma MIF concentrations were elevated in a significantly greater proportion of patients on admission (MIF 71% vs. cTnI 36% vs. myoglobin 32% vs. CK 14%, all p<0.05 compared with MIF). Admission plasma MIF concentration correlated with both day-3 and 3-month MI size (r=0.8, p<0.0001; and r=0.7, p<0.0001, respectively). Admission plasma MIF concentration was the only multivariate predictor of day-3 and 3-month MI size (both p<0.05).

The upper reference concentration of plasma MIF was 2SD above the mean calculated from control and stable CAD participants, which was 1.4 µg/L.

The infarct size at 3 days after AMI may be expressed as a percentage and may be prognosed (quantified) from the correlation:

Infarct size at 3 days (%)=6.7×admission plasma MIF concentration (µg/L)+3.0.

The infarct size at 3 months after AMI may be expressed as a percentage and may be prognosed (quantified) from the correlation:

Infarct size at 3 months (%)=5×admission plasma MIF concentration (µg/L)+1.3.

The person skilled in the art will appreciate that the magnitude of plasma MIF concentration may vary depending on the characteristics of the assay used to measure MIF (e.g. different antibodies). Nevertheless, the person skilled in the art will also appreciate that, provided the appropriate control samples are analysed, the appropriate reference plasma MIF concentration can be determined.

Accordingly, the upper reference plasma MIF concentration may be 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.5, 5.0, 5.5, 6.0, 6.5, 7.0, 7.5, 8.0, 8.5, 9.0, 9.5, 10.0 µg/L or greater.

A plasma MIF concentration is greater than a reference plasma MIF concentration when it exceeds the reference plasma MIF concentration by 10%, 15%, 20%, 25%, 30%, 35%, 40%, 45%, 50%, 55%, 60%, 65%, 70%, 75%, 80%, 85%, 90%, 95% or 100% or more. A plasma MIF concentration that exceeds the reference plasma MIF concentration by 50% is equivalent to a 1.5-fold greater plasma MIF concentration, and a plasma MIF concentration that exceeds the reference plasma MIF concentration by 100% is equivalent to a 2-fold greater plasma MIF concentration, and so on. Accordingly, a plasma MIF concentration is greater than a reference plasma MIF concentration when it is 2-fold, 2.5-fold, 3-fold, 3.5-fold, 4-fold, 4.5-fold, 5-fold, 5.5-fold, 6-fold, 6.5-fold, 7-fold, 7.5-fold, 8-fold, 8.5-fold, 9-fold, 9.5-fold, 10-fold or more than the reference plasma MIF concentration. In another embodiment, a plasma MIF concentration is greater than a reference plasma MIF concentration when it exceeds the reference plasma MIF concentration and the difference is statistically significant as determined by methods known to the person skilled in the art.

Furthermore, the prognostic correlation for calculating the magnitude of ACS, e.g. infarct size, can be readily determined by the person skilled in the art according to the present disclosure.

Plasma biomarkers have assumed a central role in the diagnosis of acute myocardial ischaemic events. The most widely used of these markers are those dependent on the release of the contraction apparatus (sarcomere) related proteins, the troponins and myocardial subfractions of troponin, which have largely supplanted the use of CK due to advantages in sensitivity and specificity. An advantage of plasma troponin measurement is that it remains elevated for up to 7 to 10 days after myocardial necrosis, which can be clinically useful in diagnosing episodes of chest pain which have occurred in the previous week. However, apparent elevation in plasma troponin due to non-coronary (non-ischaemic) causes is well known, such as due to the presence of renal failure, sepsis or heterophile antibodies. Although these limitations are important, the most significant limitation to the diagnostic value of plasma troponin measurements is the delay between the onset of the ischaemic event and the subsequent elevation in troponin value. Thus, in many cases no elevation is evident during the first 6 hours and biomarker 'rule out' of an acute MI requires serial measurements up to 8 to 12 hours after symptom onset. In contrast, plasma MIF concentration accurately diagnoses ACS, for example AMI, in less than about 4 hours after symptom onset. There is an inherent advantage in the availability of the present biomarker that can detect myocardial necrosis in the majority of patients within the first few hours of presentation to hospital, a time when plasma troponin concentrations remain within the normal range.

Most studies assessing point-of-care rule-out of ACS have employed the use of myoglobin to improve sensitivity of their diagnostic algorithm as myoglobin is an early marker for myocardial necrosis, but lacks specificity. However, admission plasma MIF concentration in the STEMI group was already elevated in a significantly higher proportion of patients compared to admission myoglobin. This suggests that MIF is of greater clinical utility than myoglobin for the purpose of improving sensitivity in the diagnosis of early myocardial necrosis, at least where large amounts of myocardial necrosis are likely to develop as in the setting of STEMI.

Experimental studies suggest that MIF is highly expressed in the infarcted and non-infarcted myocardium. While not wishing to be bound to any particular hypothesis, the early rise in plasma MIF concentration may reflect release of pre-synthesized myocardial stores, whereas the later rise in concentration may reflect production by circulating mononuclear cells although the exact source is still uncertain.

Thus, the present invention relates to a method for diagnosing ACS, a method for prognosing ACS, and a method for treating ACS.

As used herein, a "method" for diagnosing, prognosing or treating ACS in a subject comprising measuring plasma MIF concentration may be presented in an alternative form. In one example, the method may be in the form of "use" of plasma MIF concentration for diagnosing, prognosing or treating ACS in a subject. In a second example, the method may be in the form plasma MIF concentration "for use" in diagnosing, prognosing or treating ACS in a subject. In another form, the method may be in the Swiss form "use of plasma MIF concentration in the manufacture" of a diagnostic or prognostic agent or a medicament.

In a preferred embodiment, the method of diagnosis or prognosis of ACS in a subject is performed in vitro on a plasma (or serum or blood) sample that is not returned to the subject.

The method for diagnosing, prognosing or treating ACS in a subject may further comprise measuring another cardiac biomarker. In one embodiment, the method further comprises measuring plasma myoglobin, plasma troponin or plasma creatine kinase. Troponin may be troponin I, including cardiac troponin I (cTnI), or troponin T. Troponin may be measured using a highly sensitive troponin assay.

Subsequent to diagnosis or prognosis of ACS in the subject, the method may further comprise treating the subject by percutaneous coronary intervention (PCI) and/or fibrinolysis. Treatment may further comprise administration of an anti-thrombotic, anti-platelet drug, for example, a glycoprotein IIB/IIIA inhibitor (e.g. abciximab, eptifibatide, or tirofiban), or an adenosine diphosphate (ADP) receptor inhibitor (e.g. clopidogrel, prasugrel, ticagrelor, or ticlopidine).

Preferably, the sample in which MIF is measured is plasma. Plasma may be obtained by anti-coagulating blood with EDTA, sodium heparin, lithium heparin, sodium citrate or sodium oxalate. Alternatively, the sample in which MIF is measured is serum. In one embodiment, the sample is whole blood.

"Acute coronary syndrome" or "ACS" refers to a spectrum of conditions involving chest discomfort or other symptoms caused by lack of oxygen to the heart. The symptom is consequent upon erosion, fissuring or rupture of a pre-existing atherosclerotic plaque, and occurs spontaneously. In the absence of evidence of myocardial necrosis, unstable angina is diagnosed, but in the presence of evidence of myocardial necrosis (e.g. a plasma biomarker) AMI is diagnosed. Thus, ACS may comprise unstable angina or AMI. "ACS" does not include stable angina.

"Acute myocardial infarction" or "AMI" refers to the interruption of blood supply to a part of the heart, causing restriction in blood supply ("ischaemia"), lack of oxygen, and cell death ("necrosis"). This may result in damage or death of heart muscle tissue (myocardium). Thus, "myocardial necrosis" refers to the death of heart cells. AMI may be divided into ST elevation myocardial infarction (STEMI), diagnosed by elevation of the ST segment of the electrocardiogram, and non-ST elevation myocardial infarction (non-STEMI), diagnosed by absence of such electrocardiographic changes. STEM may be treated with fibrinolysis, thrombolysis or PCI. Non-STEMI may be managed with medication, although PCI is often performed during hospital admission.

A "coronary event" refers to any severe or acute cardiovascular condition including AMI, unstable angina, or cardiac mortality.

"Left ventricular hypertrophy" or "LVH" refers to thickening of the myocardium (muscle) of the left ventricle of the heart.

"Left ventricular end-diastolic volume" or "LVEDV" is defined as the volume of blood within the left ventricle immediately before contraction.

"Left ventricular end-systolic volume" or "LVESV" is defined as the volume of blood remaining within the left ventricle at the end of contraction.

"Stroke volume" is defined as the difference between LVEDV and LVESV and refers to the volume of blood ejected from the left ventricle with each contraction (heartbeat).

"Left ventricular ejection fraction" or "LVEF" is defined as the fraction of the LVEDV that is ejected with each contraction (heartbeat); that is, "stroke volume" divided by LVEDV. LVEF may be expressed as a percentage.

As used herein, "infarct size" is measured by cardiac magnetic resonance (CMR) and is defined as the area of hyperenhanced myocardium (bounded by manually traced endocardial and epicardial contours) on each short axis slice multiplied by the slice thickness and the myocardial density of 1.05 g/ml to obtain the infarct mass, and expressed as a percentage of left ventricular mass.

As used herein, "left ventricular mass indexed" refers to the left ventricular mass in g divided by the square of the height in m of a subject, and is expressed in units $g/m^2$.

As used herein, "biomarker" refers to a measurable substance, detection of which indicates a particular cardiac disease. A "biomarker" may indicate a change in expression or state of the measurable substance that correlates with the prognosis of a disease. A "biomarker" may be a protein or peptide. A "biomarker" may be measured in a bodily fluid such as plasma. As used herein, the "biomarker" is plasma macrophage migration inhibitory factor (MIF). In one embodiment, MIF is full-length. In another embodiment, MIF is a fragment thereof.

Preferably, MIF is human MIF for clinical diagnosis and comprises the amino acid sequence provided as NCBI Reference Sequence: NP_002406.1 (SEQ ID NO: 1):

MPMFIVNTNVPRASVPDGFLSELTQQLAQATGKPPQYIAVHVVPDQLMAF

GGSSEPCALCSLHSIGKIGGAQNRSYSKLLCGLLAERLRISPDRVYINYY

DMNAANVGWNNSTFA

Alternatively, MIF may be from another mammal, for example primate, murine, bovine, ovine, equine, porcine, canine or feline, for veterinarian diagnosis.

As used herein, "diagnosis" and similar terms refer to the identification of ACS. In particular, measurement of plasma MIF concentration enables diagnosis of ACS.

As used herein, "prognosis" and related terms refer to the description of the likely outcome of ACS. Furthermore, measurement of plasma MIF concentration may quantify the ACS, thereby enabling prognosis of the ACS.

Diagnosis and prognosis may be used in tandem. For example, in a subject with suspected AMI, measurement of plasma MIF concentration enables identification of AMI (diagnosis), and because plasma MIF concentration correlates with the magnitude of AMI (e.g. quantification of infarct size), plasma MIF concentration enables description of the likely morbidity and mortality arising from the infarct (prognosis). In one embodiment, the method of the first aspect further comprises prognosing ACS. In one embodiment of the second aspect, diagnosis and/or prognosis may be made from a sample taken from the subject less than 4 hours after symptom onset.

As used herein, "onset of symptoms" or "symptom onset" is the time at which a subject begins to experience a departure from normal physiology.

As used herein, "admission" refers to the formal acceptance by a hospital or other health care facility of a subject who is to be provided with medical treatment. In particular, "admission" will be associated with an accurate time at which the subject is accepted for medical treatment.

As used herein, "admission plasma MIF concentration" refers to the MIF concentration measured in plasma derived from a blood sample obtained as soon as practicable after admission, but less than 4 hours after symptom onset. Alternatively, "admission plasma MIF concentration" may refer to the MIF concentration measured in plasma derived from a blood sample obtained 210 minutes, 180 minutes, 150 minutes, 120 minutes, 110 minutes, 100 minutes, 90 minutes, 80 minutes, 70 minutes, 60 minutes, 50 minutes, 40 minutes, 30 minutes, 20 minutes, 10 minutes or 5 minutes or less after symptom onset.

If a subject has not been accepted for medical treatment, but is at home or place of work for example, "admission plasma MIF concentration" is understood to mean less than 240 minutes, or 210 minutes, 180 minutes, 150 minutes, 120 minutes, 110 minutes, 100 minutes, 90 minutes, 80 minutes, 70 minutes, 60 minutes, 50 minutes, 40 minutes, 30 minutes, 20 minutes, 10 minutes or 5 minutes or less after symptom onset.

The time at which a sample may be taken from a subject is applicable to all aspects of the invention, in particular the first, second and third aspects of the invention.

As used herein, "means for measuring" plasma MIF refers to any mechanism by which MIF can be detected and measured (assayed or quantified).

Plasma MIF may be detected and measured in a sample using any method known to those skilled in the art for detecting proteins including, but not limited to, for example immunoassays such as, for example ELISA, enzyme immunoassay (EIA), Western blot, slot blot, dot blot, or immunoprecipitation followed by sodium dodecyl sulfate polyacrylamide gel electrophoresis, (SDS-PAGE), chromatography and the like. Dendrimer-enhanced radial partition immunoassays and immunofluorescence assays, for example, are known in the art and are commercially available.

As used herein, "assay", and variants thereof, refers to measurement or quantification of the concentration of plasma MIF.

One exemplary agent for detecting a protein of interest is an antibody, or fragment thereof, capable of specifically binding to plasma MIF. The antibody may detectably labelled, either directly or indirectly.

Anti-MIF antibodies are commercially available from suppliers such as Abcam and include: chicken polyclonal anti-MIF antibody (ab34644); goat polyclonal anti-MIF antibody (ab36146, ab14574); rabbit polyclonal anti-MIF (C-terminus) antibody (ab65869); rabbit polyclonal anti-MIF antibody (ab86670); mouse monoclonal anti-MIF antibody (ab55445); and mouse anti-MIF monoclonal antibody [2Ar3] (ab14575).

Immunoassays for plasma MIF may comprise incubating a sample with a detectably labelled antibody, or antibody fragment, capable of specifically binding plasma MIF, and detecting the bound antibody by any of a number of techniques well-known in the art. As discussed in more detail, below, the term "labelled" can refer to direct labelling of the antibody via, e.g., coupling (i.e., physically linking) a detectable substance to the antibody, and can also refer to indirect labelling of the antibody by reactivity with another reagent that is directly labelled. An example of indirect labelling includes detection of a primary antibody using a fluorescently labelled secondary antibody.

The sample can be brought in contact with and immobilised on a solid support or carrier, or other solid support, which is capable of immobilising soluble proteins. The support can then be washed with suitable buffers followed by treatment with the detectably labelled antibody. The solid support can then be washed with the buffer a second time to remove unbound antibody. The amount of bound label on solid support can then be detected by conventional methods.

By "solid support or carrier" is intended any support capable of binding an antigen or an antibody. Well-known supports or carriers include nitrocellulose, glass, polystyrene, polypropylene, polyethylene, dextran, nylon, amylases, natural and modified celluloses, polyacrylamides and magnetite. The nature of the solid support or carrier can be either soluble to some extent or insoluble. The solid support can have virtually any possible structural configuration so long as the coupled molecule is capable of binding to an antigen or antibody. Thus, the support configuration can be spherical, as in a bead, or cylindrical, as in the inside surface of a test tube, or the external surface of a rod. Alternatively, the surface can be flat such as a sheet, test strip, etc. Those skilled in the art will know many other suitable carriers for binding antibody or antigen, or will be able to ascertain the same by use of routine experimentation.

One of the ways in which an antibody specific for plasma MIF can be detectably labelled is by linking the antibody to an enzyme for use in an enzyme immunoassay. The enzyme bound to the antibody will react with an appropriate substrate, preferably a chromogenic substrate, in such a manner as to produce a chemical moiety which can be detected, for example, by spectrophotometric, fluorimetric or by visual means. Enzymes that can be used to detectably label the antibody include, but are not limited to, malate dehydrogenase, staphylococcal nuclease, delta-5-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection and measurement can be accomplished by colorimetric methods which employ a chromogenic substrate for the enzyme. Detection and measurement can also be accomplished by visual comparison of the extent of enzymatic reaction of a substrate in comparison with similarly prepared standards.

Detection and measurement can also be accomplished using any of a variety of other immunoassays. For example, by radioactively labelling the antibody or functional antibody fragment, it is possible to detect plasma MIF through the use of a radioimmunoassay (RIA). The radioactive isotope (e.g., $^{125}$I, $^{131}$I, $^{35}$S, $^{32}$P or $^3$H) can be detected by such means as the use of a gamma counter or a scintillation counter or by autoradiography.

It is also possible to label the antibody with a fluorescent or luminescent compound. When the fluorescently labelled antibody is exposed to light of the appropriate wavelength, its presence can then be detected due to fluorescence. Among the most commonly used fluorescent labelling compounds are fluorescein isothiocyanate, rhodamine, phycoerythrin, phycocyanin, allophycocyanin, o-phthaldehyde and fluorescamine.

The antibody can also be detectably labelled using fluorescence emitting metals such as $^{152}$Eu, or others of the lanthanide series. These metals can be attached to the antibody using such metal chelating groups as diethylenetriaminepentacetic acid (DTPA) or ethylenediaminetetraacetic acid (EDTA).

Fluorescence energy transfer compounds may also be employed.

The antibody also can be detectably labelled by coupling it to a chemiluminescent compound. The presence of the chemiluminescent-tagged antibody is then determined by detecting the presence of luminescence that arises during the course of a chemical reaction. Examples of particularly useful chemiluminescent labelling compounds are luminol, isoluminol, theromatic acridinium ester, imidazole, acridinium salt and oxalate ester. Likewise, a bioluminescent compound can be used to label the antibody. Bioluminescence is a type of chemiluminescence found in biological systems in, which a catalytic protein increases the efficiency of the chemiluminescent reaction. The presence of a bioluminescent protein is determined by detecting the presence of luminescence. Important bioluminescent compounds for purposes of labelling are luciferin, luciferase and aequorin.

In another embodiment, specific binding molecules other than antibodies, such as aptamers, may be used to bind plasma MIF.

Other "means for measuring" plasma MIF include chromatography or electrophoresis with dye-based detection, or proteomics approaches employing spectrometry such as mass spectrometry. Spectrometry may be used to measure dye-based assays, including visible dyes, and fluorescent or luminescent agents.

A protein chip assay may be used to measure plasma MIF.

Plasma MIF can also be measured or assayed using of one or more of the following methods. For example, methods may include nuclear magnetic resonance (NMR) spectroscopy, a mass spectrometry method, such as electrospray ionization mass spectrometry (ESI-MS), ESI-MS/MS, ESI-MS/(MS)n (n is an integer greater than zero), matrix-assisted laser desorption ionization time-of-flight mass spectrometry (MALDI-TOF-MS), surface-enhanced laser desorption/ionization time-of-flight mass spectrometry (SELDI-TOF-MS), desorption/ionization on silicon (DIOS), secondary ion mass spectrometry (SIMS)3 quadrupole time-of-flight (Q-TOF), atmospheric pressure chemical ionization mass spectrometry (APCI-MS), APCI-MS/MS, APCI-(MS), atmospheric pressure photoionization mass spectrometry (APPI-MS), APPI-MS/MS, and APPI-(MS). Other mass spectrometry methods may include quadrupole, Fourier transform mass spectrometry (FTMS) and ion trap. Other suitable methods may include chemical extraction partitioning, column chromatography, ion exchange chromatography, hydrophobic (reverse phase) liquid chromatography, isoelectric focusing, one-dimensional polyacrylamide gel electrophoresis (PAGE), two-dimensional polyacrylamide gel electrophoresis (2D-PAGE) or other chromatography, such as thin-layer, gas or liquid chromatography, or any combination thereof.

In one embodiment, LDI-TOF-MS allows the generation of large amounts of information in a relatively short period of time. A biological sample is applied to one of several varieties of a support that binds MIF in the sample. Samples are applied directly to these surfaces in volumes as small as 0.5 μL, with or without prior purification or fractionation. The sample can be concentrated or diluted prior to application onto the support surface. Laser desorption/ionization is then used to generate mass spectra of the sample in as little as three hours.

A bead assay may be used to measure plasma MIF.

As used herein, "device" refers to a physical arrangement of components for performing an assay for measuring plasma MIF. The device may be a point-of-care device used by a medical practitioner to measure plasma MIF without the need for laboratory measurement. Alternatively, a point-of-care device may be used domestically, for example in a subject at risk of a first or subsequent coronary event. Alternatively, the device may be in a laboratory located separately to the subject in whom plasma MIF is to be measured.

The device may employ an electrochemical cell. Electrochemical cells may use electrodes positioned within the cell in a side-by-side or "coplanar" layout to minimize the electrical interference between the electrodes. Alternatively, electrochemical cells may use non coplanar electrodes that exploit the electrical interference between the electrodes to yield additional information about the sample including information that can correct for patient to patient variations in hematocrit and interfering chemical substances that may be present in a sample.

In one embodiment, the device also measures plasma myoglobin, plasma troponin and/or plasma creatine kinase. In one embodiment, the device measures C-reactive protein (CRP) using a highly sensitive CRP assay.

The device may provide a qualitative output (e.g. yes/no, presence/absence/, high/low), a numerical or quantified output (e.g. concentration), or an output for visual inspection (e.g. a colour for comparison with a reference scale).

As used herein, "kit" refers to a physical arrangement of components, one of which may be the device for measuring plasma MIF. The kit may include a reagent such as an anti-MIF immunogenic moiety, a secondary detection agent for detecting the immunogenic moiety, or a reagent for sample preparation and/or processing, for example a buffer. The kit may include means, such as reagents, to perform a highly sensitive CRP assay.

The device or kit may be accompanied by instructions or directions for use of the device or kit in a method for: (a) diagnosing ACS in the subject, the method comprising measuring plasma MIF concentration in the sample taken from the subject less than 4 hours after symptom onset, and diagnosing ACS when the subject plasma MIF concentration is greater than a reference plasma MIF concentration; or (b) prognosing ACS in the subject, the method comprising measuring plasma MIF concentration in the sample, diagnosing ACS when the subject plasma MIF concentration is greater than a reference plasma MIF concentration, and prognosing the magnitude of ACS from the subject plasma MIF concentration.

As used herein, a device or kit may be in alternative forms. One form designates either suitability for or restriction to a specific use and is indicated by the word "for". Another form is restricted to a specific use only and is indicated by the words "when used for" or similar.

In one embodiment of the method for diagnosing or treating ACS in a subject, plasma MIF is measured using the device disclosed herein.

As used herein, "sensitivity" refers to the ability to identify positive results. "Sensitivity" is calculated as the number of true positives in a sampled divided by the sum of the number of true positives plus the number of false negatives.

As used herein, "specificity" refers to the ability to identify negative results. "Specificity" is calculated as the number of true negatives in a sampled divided by the sum of the number of true negatives plus the number of false positives.

As used in the subject specification, the singular forms "a", "an" and "the" include plural aspects unless the context clearly dictates otherwise. Thus, for example, reference to "a luminescent material" includes a single luminescent material, as well as two or more luminescent materials and so forth.

In the claims which follow and in the description of the invention, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

It will be apparent to the person skilled in the art that while the invention has been described in some detail for the purposes of clarity and understanding, various modifications and alterations to the embodiments and methods described herein may be made without departing from the scope of the inventive concept disclosed in this specification.

An embodiment exemplified for any aspect of the invention is applicable to any other aspect of the invention. In other words, any embodiment exemplified for any aspect of the invention is not to be limited only to that particular aspect of the invention.

EXAMPLE

The invention is now further described in detail by reference to the following example. The example is provided for purposes of illustration only, and is not intended to be limiting unless otherwise specified. Thus, the invention encompasses any and all variations which become evident as a result of the teaching provided herein.

Methods
Study Participants

Study participants were enrolled from a concurrent investigator-led trial assessing the effects of iron chelation with desferrioxamine on infarct size in patients with STEMI. Briefly, consecutive patients>18 years of age with first presentation STEMI with chest pain≥30 minutes in duration, symptom onset<6 hours, and electrocardiographic changes of new ischemia (ST elevation at the J point≥0.1 mV in 2 contiguous leads) were invited to participate. All patients having one or more of the following criteria were excluded: an intracardiac device not compatible with CMR (e.g. pacemaker); suspected or known previous MI in the same coronary artery territory as the current STEMI; rescue angioplasty; cardiogenic shock (systolic blood pressure<90 mmHg); current iron supplementation or known iron deficient state; renal failure (estimated glomerular filtration rate 30 ml/min); or severe claustrophobia.

A total of 41 patients were recruited from the iron chelation study (n=20 in the iron chelation arm with desferrioxamine; and n=21 in the placebo arm) and all underwent PPCI as per routine practice. All patients had plasma sampling performed prior to any trial treatment administration and prior to PCI. CMR examination post MI was completed in all 41 patients at day 3±1 and 33 patients at 3 months.

Ten age-matched healthy volunteers without history of MI were recruited as controls. Another 9 patients with known stable CAD without prior MI in the past 12 months were also recruited as non-infarct controls during routine outpatient visits.

The study was carried out at the Alfred Hospital between August 2008 and December 2010. All patients provided written informed consent and the study was approved by the Alfred Hospital Human Research Ethics Committee in accordance with NHMRC National Statement on Ethical Conduct in Research Involving Humans.

Biochemical Analysis

All routine laboratory analyses including full blood examination, renal function, cTnI and CK were analysed immediately by the Alfred Hospital Pathology Service on commercially available automated platforms by laboratory technicians blinded to patient randomisation.

The upper reference limit for CK chosen for this study was conservatively chosen to be 200 U/L based on manufacturer recommendation, which is the $95^{th}$ percentile.

The upper reference value for myoglobin chosen for this study was 200 μg/L, based on a study by McCord et al[3] using a point-of-care test to rule out myocardial necrosis, where 200 μg/L provided the optimal cut-point for differentiating chest pain due to ACS. In this study, myoglobin was measured by in whole blood using a fluorescence immunoassay (Triage Cardiac Panel, Biosite Diagnostics).

Cardiac troponin I and myoglobin were measured on the Abbott Architect ci16200 (Abbott Laboratories, Illinois, U.S.A.) using Chemiluminescent Microparticle Immunoassay (CMIA). The lower limit of detection for troponin I was 0.03 μg/L. Concentrations below the lower detection of limit were treated as '0'. The upper reference limit for troponin I was taken as 0.05 μg/L.[1]

MIF was measured in plasma using an ELISA kit (human MIF cat #DY289) according to the manufacturer's specifications (in duplicates) and all reagents sourced form R&D ELISA kit (R&D systems, MN U.S.A.) as previously described.[2] As normal plasma values have not been previously published other than from small series from Yu and colleagues[2], the upper reference value cut-off of 2SD above the mean obtained from control and stable CAD participants was used, which was 1.4 μg/L, well above the normal values reported by Yu et al.[2]

Measurements of Left Ventricular Volumes, Function and Infarct Size by Cardiac Magnetic Resonance Imaging All CMR examinations were performed on a clinical 1.5-T CMR scanner (Signa HDx 1.5-T, General Electric Healthcare, Waukesha, Wis., USA) at the Alfred Hospital. LV function was assessed by a standard steady state free precession technique called "FIESTA" [Fast Imaging Employing Steady State Acquisition] (repetition time [TR] 3.8 ms, echo time [TE] 1.6 ms, 30 phases, and slice thickness of 8 mm). LV ejection fraction was calculated by volumetric analysis from a contiguous short axis FIESTA stack (8 mm slice thickness) covering the LV and right ventricle from the apex to a concentration well above the atrio-ventricular groove using the summation of disc method[4] by at least 2 cardiologists blinded to treatment allocation. Late enhancement images covering the whole ventricle were acquired approximately 15 minutes after intravenous administration of a bolus of gadolinium-DTPA (0.2 mmol/kg, Magnevist, Schering, Germany) to identify regional necrosis/fibrosis for infarct size quantification using an inversion recovery gradient echo technique (TR 7.1 ms, TE 3.1 ms, TI individually determined to null the normal myocardial signal, range 180-250 ms, slice thickness 8 mm, matrix 256×192, number of acquisitions=2). The area of hyperenhanced myocardium (bounded by endocardial and epicardial contours) on each of the short axis slice was manually traced then multiplied by the slice thickness and the myocardial density of 1.05 g/ml to obtain the infarct mass, and expressed as a percentage of LV mass (infarct size).[5] All analyses were performed offline on dedicated workstations running AW SDC 4.4 and IDL version 6.3 with ReportCARD version 3.6 by fully blinded observers with excellent reproducibility (r=0.98) for infarct size assessment.

Statistical Analysis

Categorical data are presented as numbers and percentages. Continuous data are presented as mean±SD unless otherwise stated. Continuous variables were compared with either
paired or un-paired Student's t-test while categorical variables were compared between groups with Pearson chi-square, Mann-Whitney or a Fisher exact test where appropriate. Correlation between continuous parameters was assessed with Pearson's correlation coefficient.

Univariate linear logistic regression was performed with day three and 3 month CMR infarct size as the dependent variable to examine the association of admission MIF, cTnI, CK and myoglobin concentrations with infarct size in a sequential approach to reduce the number of false positive results from multiple testing. Any biomarkers which emerged from the linear logistic regression with a p<0.10 were entered into a multivariate linear logistic regression model with the use of backward elimination (retention threshold, p<0.05).

Probability values<0.05 were considered statistically significant. All data analyses were performed with SPSS version 16 (SPSS Inc., Chicago, Ill., U.S.A.) and Graphpad Prism 5.0 (GraphPad Software, CA, U.S.A.).

Results

Baseline Clinical Characteristics

The baseline clinical characteristics of the study population including the 41 patients with STEMI, 9 patients with stable CAD and 10 age-matched healthy volunteers are presented in Table 1. Patients with acute MI and stable CAD were predominantly males compared to controls. Patients with stable CAD were significantly older than the STEMI and control groups (73.7±5.1 vs. 59.4±10.9 vs. 57.7±12.7, all p<0.05). A significant proportion of STEMI patients were smokers compared to the other 2 groups but there was no significant difference in other cardiovascular risk factors between STEMI and stable CAD patients.

TABLE 1

Baseline characteristics of study participants

|  | Healthy control | Stable CAD | Acute MI |
|---|---|---|---|
| N | 10 | 9 | 41 |
| Age (years) | 57.7 ± 12.7 | 73.7 ± 5.1* | 59.4 ± 10.9† |
| Gender (n, male/female) | 5/5 | 8/2 | 34/8* |
| Body mass index (kg/m$^2$) | 23.3 ± 2.1 | 28.6 ± 3.8* | 27.7 ± 5.4* |
| Current smoking (%) | 10 | 20 | 46*† |
| Hypertension (%) | — | 40 | 39 |
| Diabetes (%) | — | 30 | 15 |
| Hyperlipidaemia (%) | — | 40 | 34 |
| Family history of coronary artery disease (%) | 40 | 50 | 46 |

Values are expressed as mean ± SD or percentage.
*p < 0.05 vs. control;
†p < 0.05 vs. stable coronary artery disease (CAD).

Baseline Clinical and Procedural Characteristics of STEMI Patients

Table 2 summarizes the clinical and procedural characteristics of the STEMI patients. The median admission to blood sampling time was 70 [47-105] minutes. The mean symptom to blood sampling time was 196 minutes. Only the mean CK plasma concentration 132.5±110.7 U/L was below the upper reference limit chosen for this study (200 U/L), whereas all other admission biomarker concentrations were above the upper reference limit (cTnI 0.10±0.21 µg/L [reference range<0.05 µg/L]; myoglobin 366.6±913.3 µg/L [reference range<200 µg/L]; MIF 2.2±1.2 µg/L [reference range<1.4 µg/L]).

TABLE 2

Baseline clinical and procedural characteristics in STEMI patients

| | |
|---|---|
| Heart rate (bpm) | 73 ± 16 |
| Systolic blood pressure (mmHg) | 122 ± 23 |
| Diastolic blood pressure (mmHg) | 77 ± 14 |
| Serum creatine (µmol/L) | 85.2 ± 25.1 |
| Ischaemia time (symptom to reperfusion) (minutes) | 211 ± 75 |
| Symptom to blood sampling time (minutes) | 196 ± 74 |
| Admission to blood sampling time (minutes) | 70 [47-105] |
| Admission troponin I (µg/L) | 0.10 ± 0.21 |
| Admission creatine kinase (U/L) | 132.5 ± 110.7 |
| Admission myoglobin (µg/L) | 366.6 ± 913.3 |
| Admission MIF (µg/L) | 2.2 ± 1.2 |

TABLE 2-continued

Baseline clinical and procedural characteristics in STEMI patients

| Pre-procedural (percutaneous coronary intervention) medication, n (%) | |
|---|---|
| Aspirin | 42 (100%) |
| Clopidogrel | 22 (54%) |
| Beta-blocker | 1 (2%) |
| angiotensin-converting enzyme inhibitor/angiotensin receptor blocker | 11 (27%) |
| Statin | 4 (10%) |
| Infarct-related artery | |
| Left anterior descending artery, n (%) | 15 (37%) |
| Right coronary artery (%) | 16 (39%) |
| Left circumflex artery (%) | 10 (24%) |
| Number of stenosed vessels | 1.7 ± 0.8 |
| Stent type (bare-metal stent/drug-eluting stent) | 28/13 |

Values are expressed as mean ± SD or exact number.

Admission Biomarker Concentrations Post STEMI

FIG. 1 shows that admission plasma MIF concentrations were significantly increased (3.5-fold) compared with the two control groups. Such elevation in MIF was sustained at day 3 post-MI.

Figure 2:
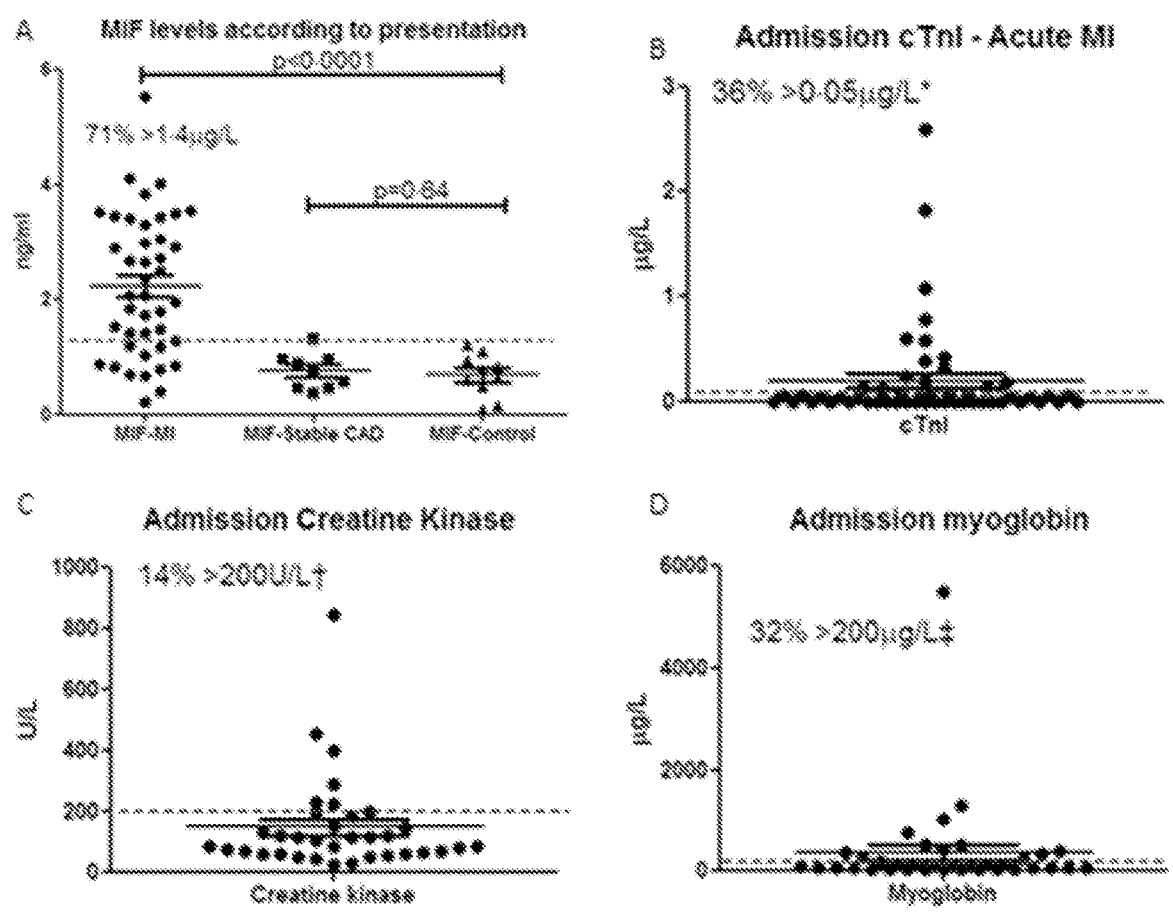
FIG. 2 depicts biomarkers admission (A) MIF, (C) CK, (B) troponin I, and (D) myoglobin concentrations compared to upper reference values for controls. Broken line denotes upper reference normal limit for respective biomarker. *p=0.002 compared to MIF; †p<0.0001 compared to MIF; ‡p=0.001 compared to MIF.

FIG. 2 shows the distribution of patients with STEMI whose admission plasma biomarker concentration was already above the upper reference limit at the first obtainable plasma sample. A significantly higher percentage of patients had MIF concentrations above the 1.4 µg/L cut-off (71%) compared to cTnI (36%), myoglobin (32%), and CK (14%), all $p<0.05$ compared to MIF.

Left Ventricular and Infarct Characteristics by CMR and Correlation with Cardiac Biomarkers CMR parameters are presented in Table 3. As expected, indexed LV mass, infarct mass and infarct size were greater at day 3 and decreased by 3 months. LV ejection improved from 48.7±7.8 to 53.8±9.4% over this time accompanied by an increase in LV end-diastolic indexed volume.

TABLE 3

Left ventricular and infarct characteristics by cardiac magnetic resonance

| CMR parameters (3 days post MI) | |
|---|---|
| LV mass indexed, (gram/m$^2$) | 76.7 ± 17.7 |
| Infarct mass, grams | 29.5 ± 23.5 |
| Infarct Size (%) | 18.5 ± 10.6 |
| LVEF (%) | 48.7 ± 7.8 |
| LVEDV indexed (ml/m$^2$) | 79.0 ± 15.8 |
| CMR parameters (3 months post MI) | |
| LV mass indexed, (gram/m$^2$) | 67.0 ± 12.9 |
| Infarct mass, grams | 16.8 ± 13.2 |
| Infarct Size (%) | 12.4 ± 8.6 |
| left ventricular ejection fraction (LVEF) (%) | 53.8 ± 9.4 |
| left ventricular end-diastolic volume (LVEDV) indexed (ml/m$^2$) | 82.5 ± 17.0 |

Values are expressed as mean ± SD or exact number.

Figure 3:
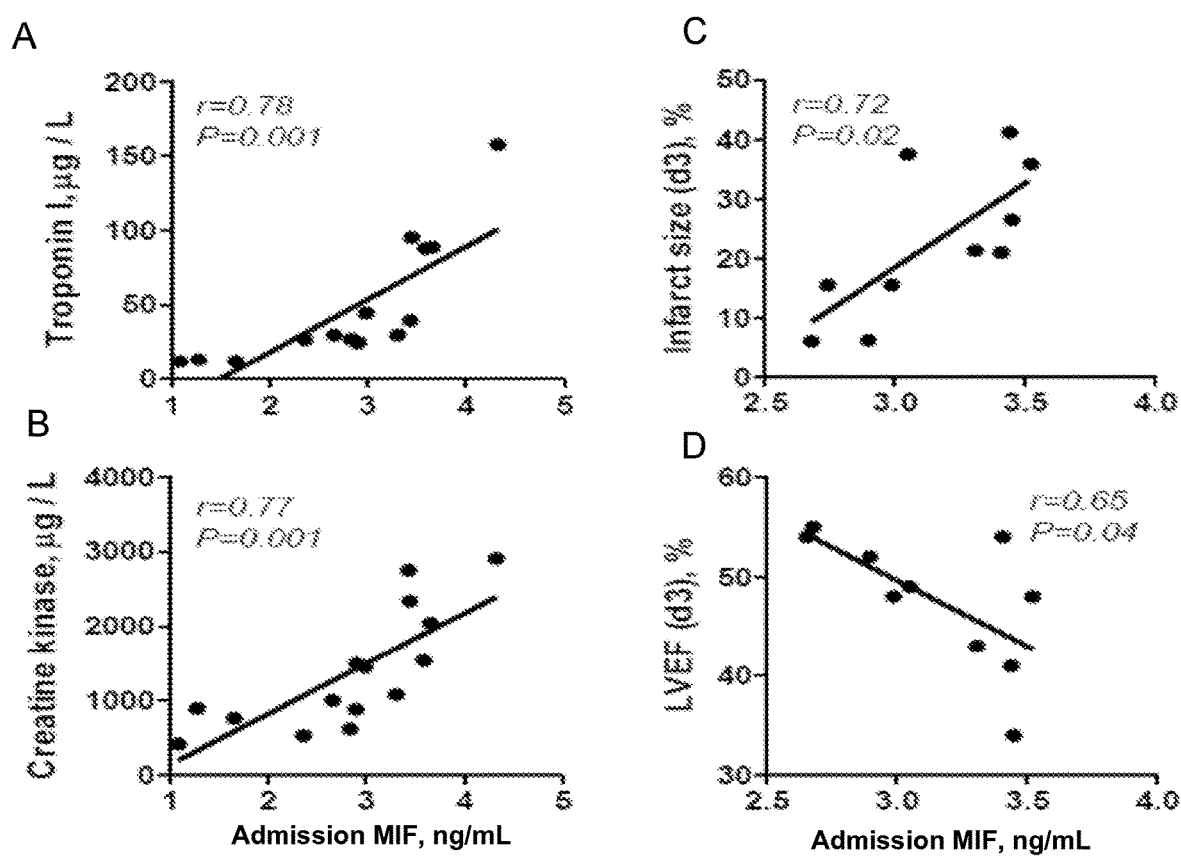
FIG. 3 depicts correlations between admission plasma MIF concentrations and admission cardiac biomarkers (A) troponin I (n=14) and (B) CK (n=15), (C) infarct size (n=10), and (D) LV function (LVEF) after AMI (n=10). Admission plasma MIF concentrations correlated positively with admission plasma concentrations of troponin I and CK. Admission plasma MIF concentrations also correlated positively with day 3 infarct size and correlated negatively with day 3 LVEF.

FIG. 3 shows that admission plasma MIF concentrations correlated positively with troponin I and CK, as well as infarct size determined by CMR. The correlation between plasma MIF concentrations and infarct size was observed only upon admission, and not between day-3 plasma MIF concentrations and infarct size (data not shown), indicating that early rise of MIF concentration in the circulation was relevant to infarct size. Further, there was a negative correlation between admission plasma MIF concentrations and LVEF measured by CMR at day 3 after AMI (FIG. 3). There was no correlation detected between MIF plasma concentrations and LV volumetric parameters (LVEDVI and LVESVI) determined by CMR.

Figure 4:
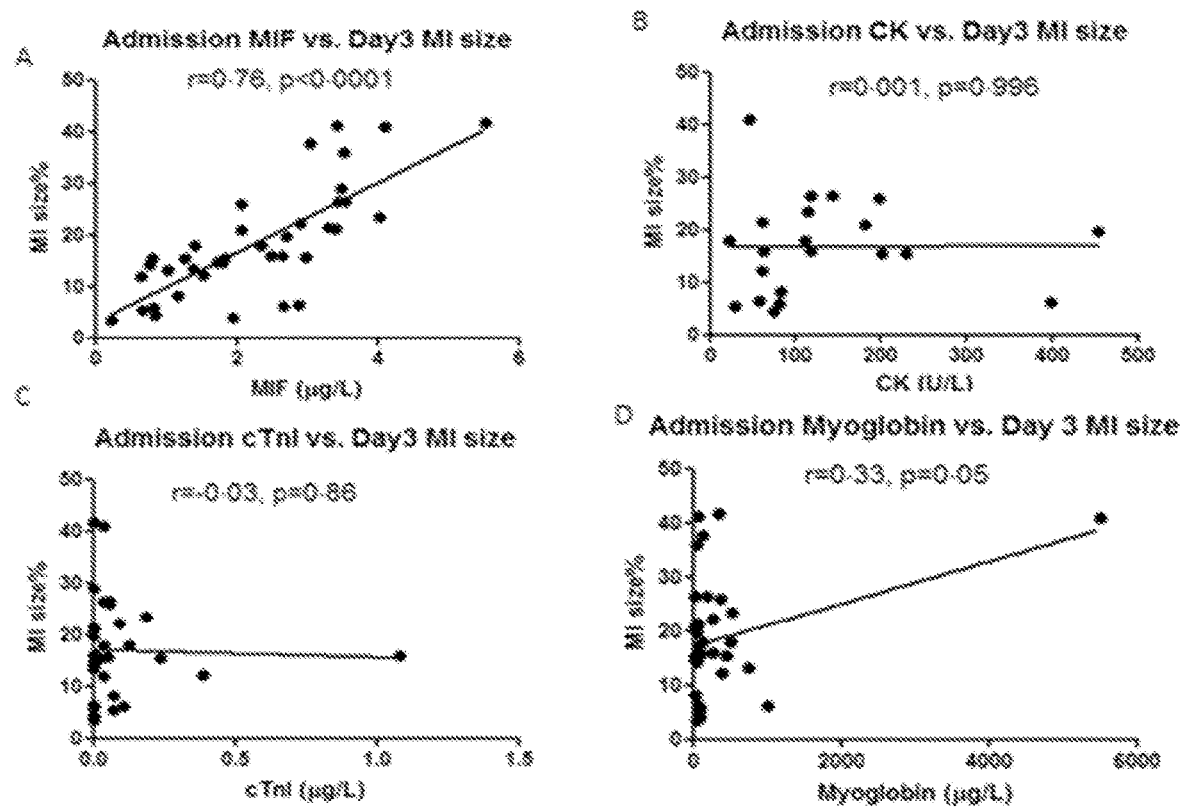
FIG. 4 depicts correlations between (A) admission plasma MIF concentrations, admission concentrations of cardiac biomarkers (B) CK, (C) troponin and (D) myoglobin, each versus day 3 MI size.
Figure 5:
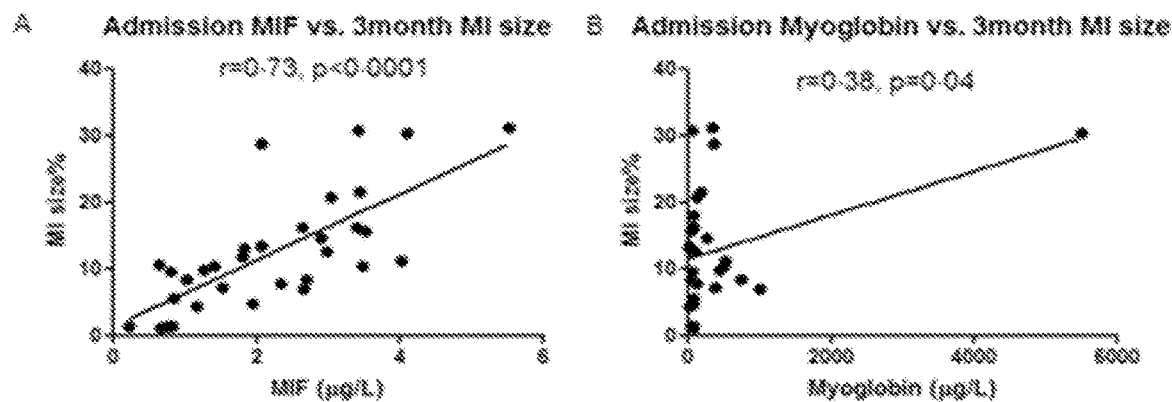
FIG. 5 depicts correlations between (A) admission plasma MIF concentrations and (B) admission concentrations of cardiac biomarker myoglobin, each versus 3 month MI size.
Figure 6:
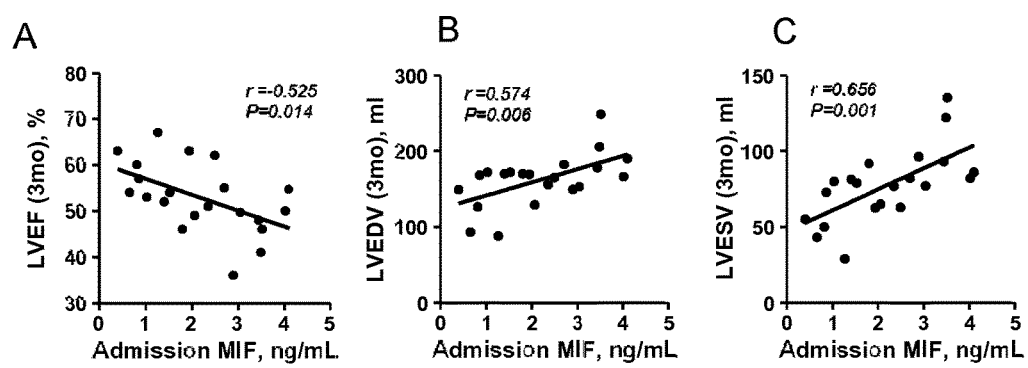
FIG. 6 depicts the correlation between admission plasma MIF concentrations and left ventricular function and dimensions (detected by cardiac magnetic resonance image), including and each of (A) left ventricular ejection fraction (LVEF), (B) left ventricular end-diastolic volume (LVEDV) and (C) left ventricular end-systolic volume. These data indicate that the admission plasma MIF concentrations predict post-MI cardiac remodelling.

Among the 4 biomarkers of myocardial necrosis, admission plasma MIF concentrations correlated best with CMR MI size on day 3 ($r=0.8$, $p<0.0001$), followed by myoglobin ($r=0.3$, $p=0.05$) (FIG. 4). Admission CK and cTnI did not correlate with day 3 MI size. At 3 months, both admission MIF and myoglobin concentrations correlated with MI size ($r=0.7$, $p<0.0001$; $r=0.4$, $p=0.04$, respectively) (FIG. 5).

Analysis of admission MIF and day 3 and 3 month MI size in patients in the placebo arm only (n=21 at day 3 and n=18 at 3 months) yielded significant correlations ($r=0.7$, $p<0.0001$; and $r=0.6$, $p=0.005$, respectively).

Analysis of the correlation between peak and cumulative release (area-under-curve [AUC]) of CK and cTnI with day 3 and 3 month MI size was also performed. The strongest correlation was observed with CK peak and day 3 MI size ($r=0.9$, $p<0.0001$), followed by cTnI peak and AUC and day 3 MI size (both $r=0.9$, $p<0.0001$) and CK peak and 3 month MI size ($r=0.8$, $p<0.0001$).

Admission Biomarker Predictors of Day 3 and 3 Month MI Size

The concentration of each of MIF, myoglobin, CK and troponin were measured in each sample taken at a median of 196 minutes after symptom onset. The four biomarkers were tested for univariate association with day-3 MI size (Table 4A). Only MIF emerged as a significant independent multivariate predictor of day-3 MI size (unstandardized coefficient (B) 4.75, 95% CI 1.70-7.81, p=0004), and 3 month MI size (4.96, 1.55-8.38, p=0.01) (Table 4B).

TABLE 4A

Univariate and multivariate predictors of day-3 MI size

| Variable | Unstandardized coefficient (B) | 95% CI | P value |
|---|---|---|---|
| MIF | 6.74 | 4.82-8.66 | <0.0001 |
| Myoglobin | 0.004 | 0.00-0.008 | 0.05 |

TABLE 4A-continued

| Creatine kinase | 0.00 | −0.04-0.04 | 0.996 |
|---|---|---|---|
| Troponin | −1.51 | −19.05-16.04 | 0.86 |
| Multivariate predictors of day 3 MI size | | | |
| Variable | Unstandardized coefficient (B) | 95% CI | p-values |
| MIF | 4.75 | 1.70-7.81 | 0.004 |

TABLE 4B

| Variable | Unstandardized coefficient (B) | 95% CI | p-values |
|---|---|---|---|
| Univariate and multivariate predictors of 3 month MI size | | | |
| MIF | 4.96 | 3.23-6.68 | <0.0001 |
| Myoglobin | 0.003 | 0.00-0.01 | 0.04 |
| Creatine kinase | 0.00 | −0.04-0.04 | 0.97 |
| Troponin | −6.77 | −44.85-31.32 | 0.72 |
| Multivariate predictors of 3 month MI size | | | |
| MIF | 4.96 | 1.55-8.38 | 0.01 |

Discussion

This prospective observational study revealed two key findings. Firstly, admission plasma MIF concentrations determined at a median of 70 minutes of presentation to hospital were already elevated in 71% of patients with STEMI compared to 36% for cTnI, 32% for myoglobin values, and only 14% for CK. Secondly, admission MIF concentrations showed a strong correlation with CMR determined infarct size at both day 3 and 3 months. Whilst peak and cumulative release CK and cTnI concentrations also showed significant correlations with MI size at both day 3 and 3 months after AMI, no significant correlation was observed between admission CK and cTnI with subsequent MI size.

In the present analysis, patients who had received iron chelation treatment (desferrioxamine) were included as well as placebo patients. All admission plasma sampling was performed prior to any study treatment and prior to PPCI, and therefore, iron chelation could not influence admission MIF concentrations. Additionally, even when analysis of admission MIF with day 3 and 3 month MI size was restricted to placebo only patients, MIF remained the only significant predictor of day 3 and 3 month MI size. All subjects underwent PPCI, which will have affected and likely reduced final infarct size. Nonetheless, initial plasma MIF concentrations remained highly predictive of in-hospital (day 3) and 3 month infarct size.

Finally, the observation that both peak and cumulative release of CK and cTnI following PPCI appear to be strong predictors of both day 3 and 3 month MI size is consistent with published literature. However, this information would not be available at least for another 12 hours for peak concentrations and 48 hours for AUC. A comparison between admission MIF and peak or cumulative CK or cTnI would not be appropriate in this context. Currently, no admission biomarkers appear to be able to predict final MI size when used within the first hours of onset of symptoms. The current study indicates that plasma MIF concentrations may offer such potential.

CONCLUSION

It is disclosed herein that plasma MIF concentrations were elevated in the majority of STEMI patients at the first obtainable sample post admission, demonstrating superior diagnostic accuracy compared to myoglobin, cTnI and CK. Admission plasma MIF concentrations predicted final infarct size at 3 days and 3 months post AMI and may have significant implications for patient management and healthcare utilisation. In summary, measurement of admission plasma MIF concentration has significant advantages over troponin for the very early detection of myocardial necrosis and prediction of infarct size.

REFERENCES

1. Than M, Cullen L, Reid C M, et al. A 2-h diagnostic protocol to assess patients with chest pain symptoms in the Asia-Pacific region (ASPECT): a prospective observational validation study. Lancet. 2011; 377(9771): 1077-84.
2. Yu C M, Lau C P, Lai K W, et al. Elevation of plasma concentration of macrophage migration inhibitory factor in patients with acute myocardial infarction. Am J. Cardiol. 2001; 88(7): 774-7.
3. McCord J, Nowak R M, McCullough P A, et al. Ninety-minute exclusion of acute myocardial infarction by use of quantitative point-of-care testing of myoglobin and troponin I. Circulation. 2001; 104(13): 1483-8.
4. Ganame J, Messalli G, Dymarkowski S, et al. Impact of myocardial haemorrhage on left ventricular function and remodelling in patients with reperfused acute myocardial infarction. Eur Heart J. 2009; 30(12): 1440-9.
5. Piot C, Croisille P, Staat P, et al. Effect of cyclosporine on reperfusion injury in acute myocardial infarction. N Engl J. Med. 2008; 359(5): 473-81.

The invention claimed is:

1. A method of treating acute myocardial infarction (AMI) in a subject, the method comprising:
   (a) measuring plasma macrophage migration inhibitory factor (MIF) concentration in a sample taken from a subject less than 4 hours after symptom onset;
   (b) determining infarct size from the subject plasma MIF concentration; and
   (c) performing percutaneous coronary intervention (PCI) and/or fibrinolysis on the subject to limit infarct size,
   wherein PCI and/or fibrinolysis is performed on the subject when the plasma MIF concentration is 1.4 μg/L or greater, and
   wherein the subject from which the sample was taken presents with at least one symptom of AMI,
   thereby treating AMI in the subject.

2. The method of claim 1, wherein the AMI is non-ST elevation myocardial infarction (non-STEMI).

3. The method of claim 1, comprising measuring plasma MIF concentration in a sample of the subject taken 3 hours or less after symptom onset.

4. The method of claim 1, comprising measuring plasma MIF concentration in a sample of the subject taken 2 hours or less after symptom onset.

5. The method of claim 1, comprising measuring plasma MIF concentration in a sample of the subject taken 1 hour or less after symptom onset.

6. The method of claim 1, comprising measuring plasma MIF concentration in a sample of the subject taken 30 minutes or less after symptom onset.

7. The method of claim 1, wherein the AMI is ST elevation myocardial infarction (STEMI).

8. The method of claim 1, further comprising measuring the subject's plasma myoglobin, plasma troponin or plasma creatine kinase concentration.

9. The method of claim 1, wherein MIF and any one or more of myoglobin, troponin or creatine kinase concentrations are measured in the same plasma sample.

* * * * *